(12) United States Patent
Knollenberg et al.

(10) Patent No.: US 10,371,620 B2
(45) Date of Patent: Aug. 6, 2019

(54) AUTOMATIC POWER CONTROL LIQUID PARTICLE COUNTER WITH FLOW AND BUBBLE DETECTION SYSTEMS

(71) Applicant: PARTICLE MEASURING SYSTEMS, INC., Boulder, CO (US)

(72) Inventors: Brian Knollenberg, Boulder, CO (US); Jim Lumpkin, Boulder, CO (US); Brett Haley, Boulder, CO (US); Matt Soappman, Boulder, CO (US); Dan Rodier, Boulder, CO (US); Mark Lilly, Boulder, CO (US)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 0 days.

(21) Appl. No.: 15/600,418

(22) Filed: May 19, 2017

(65) Prior Publication Data

US 2017/0356838 A1    Dec. 14, 2017

Related U.S. Application Data

(60) Provisional application No. 62/339,694, filed on May 20, 2016.

(51) Int. Cl.
*G01N 15/14* (2006.01)
*G01N 15/06* (2006.01)
*G01N 15/02* (2006.01)
*G01F 1/704* (2006.01)
(Continued)

(52) U.S. Cl.
CPC ......... *G01N 15/1425* (2013.01); *G01F 1/704* (2013.01); *G01N 15/0205* (2013.01); *G01N 15/06* (2013.01); *G01N 15/1459* (2013.01); *G01N 2015/0011* (2013.01);
(Continued)

(58) Field of Classification Search
CPC ........... G01N 15/1425; G01N 15/0205; G01N 15/1459; G01N 15/06; G01N 2015/0011; G01N 2015/1486; G01N 2015/0693; G01F 1/705; H05B 37/0227
See application file for complete search history.

(56) References Cited

U.S. PATENT DOCUMENTS 3,768,084 A   10/1973  Haynes
3,851,169 A   11/1974  Faxvog
4,348,111 A    9/1982  Goulas et al.
(Continued)

OTHER PUBLICATIONS

Beckman Coulter Life Science, "Reducing Bubble Contamination in Particle Count Results Using Pressure", www.azom.com, Beckman Coulter, Inc.—Particle Characterization, Date added Aug. 30, 2014 | Updated Feb. 11, 2015.
(Continued)

*Primary Examiner* — Sang H Nguyen
(74) *Attorney, Agent, or Firm* — Leydig, Voit & Mayer, Ltd.

(57) ABSTRACT

The systems and methods provided herein relate generally to the improvement of data quality in optical liquid particle counters and control of optical particle counters to achieve longer expected lifetime, for example by avoiding damage caused by electromagnetic radiation and heat. The systems and methods incorporate sensors which characterize the fluid flowing through the flow cell, thereby enhancing accuracy and reducing the number of false positives.

14 Claims, 6 Drawing Sheets

(51) Int. Cl.
*G01N 15/00* (2006.01)
*H05B 37/02* (2006.01)

(52) U.S. Cl.
CPC ........ *G01N 2015/0693* (2013.01); *G01N 2015/1486* (2013.01); *H05B 37/0227* (2013.01)

(56) References Cited

U.S. PATENT DOCUMENTS

| | | | |
|---|---|---|---|
| 4,728,190 A | | 3/1988 | Knollenberg |
| 4,957,363 A | | 9/1990 | Takeda et al. |
| 5,085,500 A | | 2/1992 | Blesener |
| 5,106,187 A | * | 4/1992 | Bezanson .......... G01N 15/1429 356/337 |
| 5,121,988 A | | 6/1992 | Blesener et al. |
| 5,282,151 A | | 1/1994 | Knollenberg |
| 5,467,188 A | | 11/1995 | Miyashita |
| 5,561,515 A | * | 10/1996 | Hairston .................. G01P 5/22 356/28 |
| 5,583,635 A | * | 12/1996 | Miura .................... G01N 15/14 356/338 |
| 5,642,193 A | | 6/1997 | Girvin et al. |
| 5,864,399 A | | 1/1999 | Girvin et al. |
| 5,920,388 A | | 7/1999 | Sandberg et al. |
| 5,946,092 A | | 8/1999 | DeFreez et al. |
| 6,200,820 B1 | * | 3/2001 | Hansen ................ G01N 15/14 435/6.1 |
| 6,317,511 B1 | * | 11/2001 | Horiuchi ............ G01N 15/1459 356/39 |
| 6,859,277 B2 | | 2/2005 | Wagner et al. |
| 7,030,980 B1 | | 4/2006 | Sehler et al. |
| 7,053,783 B2 | | 5/2006 | Hamburger et al. |
| 7,088,447 B1 | | 8/2006 | Bates et al. |
| 7,553,453 B2 | * | 6/2009 | Gu .................... B01L 3/502715 422/537 |
| 7,576,857 B2 | | 8/2009 | Wagner |
| 8,800,383 B2 | | 8/2014 | Bates |
| 2005/0229716 A1 | * | 10/2005 | Unsworth ................ G01F 1/66 73/861.53 |
| 2008/0137065 A1 | * | 6/2008 | Oberreit ................. G01N 30/84 356/37 |
| 2009/0051350 A1 | * | 2/2009 | Becker ............... G01N 15/0656 324/204 |
| 2009/0128810 A1 | * | 5/2009 | Bates ................. G01N 15/1012 356/336 |
| 2009/0268202 A1 | | 10/2009 | Wagner |
| 2014/0001050 A1 | | 1/2014 | Huang et al. |
| 2014/0225005 A1 | * | 8/2014 | Yamasaki .......... G01N 15/1459 250/459.1 |
| 2015/0211977 A1 | * | 7/2015 | Sekimoto ............... G01N 15/10 356/338 |
| 2016/0067531 A1 | | 3/2016 | Pariseau et al. |

OTHER PUBLICATIONS

HIAC 9703+ Liquid Particle Counter, www.hach.com, accessed Feb. 10, 2016.
Wang, Xiaoliang et al., "Particle Monitoring in Liquids: Liquid Particle Counter", Lab Report, University of Minnesota, Apr. 14, 2002, pp. 1-16.
U.S. Patent Office, International Search Report and Written Opinion issued in PCT/US2017/033614, dated Oct. 20, 2017.

* cited by examiner

AUTOMATIC POWER CONTROL LIQUID PARTICLE COUNTER WITH FLOW AND BUBBLE DETECTION SYSTEMS

CROSS-REFERENCE TO RELATED APPLICATIONS

This application claims priority to and the benefit of U.S. Provisional Patent Application No. 62/339,694 filed May 20, 2016, which is hereby incorporated by reference in its entirety to the extent not inconsistent herewith.

BACKGROUND OF INVENTION

This invention is in the field of optical liquid particle analyzers. In an embodiment, this invention relates generally to systems and methods for improving data quality and protecting optical components, such as a laser, photodetector, or optical lens elements from damage caused by overheating. In an embodiment, this invention also relates generally to methods and systems for adjusting optical source intensity and acquisition of data during periods in which bubbles are present in the particle analyzer and/or periods in which the fluid is either not flowing or flowing at an optimal rate.

A large portion of the micro-contamination industry and clean manufacturing industries is reliant on the use of optical particle counters, such as are described in a number of U.S. Patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. Particle counters are also described in U.S. Pat. Nos. 4,728,190, 5,282,151, 6,859,277, and 7,030,980, which are hereby incorporated by reference in their entirety.

Optical liquid particle sensors and counters are useful in a variety of industrial applications including in semiconductor, pharmaceutical and microelectronics industries. In some industrial settings, optical liquid particle sensors and counters provide an important tool for continuously monitoring the composition and purity of liquids used in a process, for example, in the production of pharmaceutical products subject to stringent regulatory requirements relating to particulate contaminants. In other industrial settings, optical liquid particle sensors and counters provide an important tool for providing quality control analysis. It is particularly advantageous to rapidly identify when a fluid is contaminated with unwanted particles so that the process can be stopped at an early stage, thereby avoiding wasteful manufacture of defective product. For example, in semiconductor and other clean-room settings, or industries requiring sterile and pure production (e.g., pharmaceuticals), material liquids that are used to make the end products are continuously monitored to ensure adequate purity and that any unwanted particles suspended in the fluid are within an acceptable tolerance range.

An issue with modern liquid particle counters is damage to internal components of the liquid particle counter, such as the detector array or the optical source, caused by changes in flow rates or bubbles in the flow chamber of the particle counter, especially in systems that utilize a high powered optical source in order to detect smaller particles. For example, when bubbles, which may be orders of magnitude larger than the particles of interest, pass through the flow chamber they scatter a large amount of electromagnetic radiation which can overload and damage the collection and detection systems of the particle counter. Additionally, if the flow rate of the liquid through the flow chamber of the particle counter is too low or stopped, the optical source may boil the liquid which scatters intense radiation throughout the particle viewing flow chamber and into the optical system, damaging the collection and detection systems and/or overheating and damaging the optical source itself.

Bubbles and changes in flow rate through the liquid particle counter also cause data integrity issues. For example, presently available optical liquid particle counters cannot distinguish between a bubble and a solid particle as they both obscure, scatter or emit electromagnetic radiation. Therefore, as bubbles pass through the flow chamber of a liquid particle counter they are falsely counted as solid particles, artificially raising the reported contamination of the system being analyzed. Further, liquid particle counters are calibrated for a specific flow rate or a range of flow rates. Changes in the flow rate through the system, either increases or decreases, alter the way in which particles obscure, scatter or emit electromagnetic radiation as they pass through the flow chamber. Thus, a non-optimized or non-normal flow rate can cause the particle counter to mischaracterize the particles, for example, by miscounting or mischaracterizing the size of the particles.

It can be seen from the foregoing that there remains a need in the art for improved liquid particle counters which reduce or eliminate damage to internal components due to flow issues or bubbles within the flow chamber. Further, there remains a need for liquid particle counters with improved resolution and reliability which account for false positives caused by bubbles and mischaracterizations caused by changes in flow rate.

SUMMARY OF THE INVENTION

The systems and methods provided herein relate generally to the improvement of data quality in optical liquid particle counters and control of optical particle counters to achieve longer expected lifetime, for example by avoiding damage caused by electromagnetic radiation and heat. The systems and methods incorporate sensors which characterize the fluid flowing through the flow cell, thereby enhancing accuracy and reducing the number of false positives. The systems and methods detect conditions which may damage components of the particle counter and prevent or minimize potential damage to the system by reducing or eliminating the amount of electromagnetic radiation entering the flow cell or the detection system of the particle counter. Further provided herein, are methods and systems for reducing the amount and size of bubbles prior to entering the flow chamber of a liquid particle counter. The systems and methods are versatile and may be used with a variety of sensors for detecting bubbles or flow rate, including sensors positioned upstream or downstream from the detection zone. In embodiments, for example, the optical particle counter alters the amount of power provided to the optical source upon detection of a change in flow rate or the presence of bubbles. In an embodiment, for example, the particle counter reduces the amount of electromagnetic energy supplied to the flow chamber, for example, by reflecting, refracting, diffusing or blocking the beam of electromagnetic radiation, either from entering the flow chamber or from reaching the collection or detection systems. In embodiments, data recorded during a period of changed flow rate or bubbles is flagged, disregarded or modified.

The provided systems and methods are versatile and may be implemented in a variety of liquid particle counters, including, for example: scattering optical particle counters, emitting optical particle counters, obscuring optical particle counters, and particle counters having one- or two-dimensional photodetector arrays. The systems and methods utilize additional external sensors, either upstream or downstream from the particle counter, or include sensors within the particle counter to detect bubbles and/or determine flow rate.

In an aspect, provided is an optical liquid particle counter system comprising: (i) a liquid particle counter comprising: a) a flow chamber for flowing a liquid containing particles along a flow direction through a beam of electromagnetic radiation, b) an optical source, in optical communication with the flow chamber, for providing the beam of electromagnetic radiation; and c) an optical collection system for collecting and directing at least a portion of electromagnetic radiation onto a photodetector; wherein the photodetector produces an electric signal characteristic of the number and/or size of the particles detected; (ii) a fluid monitoring system in fluid communication with the flow chamber that detects bubbles in the liquid, a flow rate condition of the liquid, or both bubbles and a flow rate condition; and (iii) a processor in operational communication with the fluid monitoring system and the optical liquid particle counter, wherein the processor receives monitoring data from the fluid monitoring system and provides a control signal to the optical liquid particle counter or a component thereof to decrease the power of the optical source, thereby resulting in an beam of electromagnetic radiation characterized by a lower power. In some embodiments, for example, a lower power is in reference to normal operating power, for example, reducing the fluence of electromagnetic radiation entering the flow chamber by at least 25%, at least 33% or, optionally, at least 50%. In some embodiments, flow rate condition refers to an increase or decrease in flow rate, for example, a change in flow rate of greater than 10%, 25%, or optionally, 50%. In embodiments, flow rate condition refers to a change in type of flow rate (e.g. a normal flow rate, a low flow rate, a flow stoppage or a high flow rate) to another type of flow rate. In embodiments, flow rate condition may refer to a type of flow rate, for example, a low flow rate (with respect to a flow rate for which the particle counter is calibrated or designed), a high flow rate, a normal flow rate, or a flow stoppage. In some embodiments, for example, a flow rate condition is a difference in flow rate of greater than or equal to 25%, 33% or 50% of the normal flow rate of the liquid particle counter. Flow rate condition may also refer to a stopped flow rate or a flow rate substantially close to zero.

In an aspect, provided is an optical liquid particle counter system comprising: (i) a liquid particle counter comprising: a) a flow chamber for flowing a liquid containing particles along a flow direction through a beam of electromagnetic radiation, b) an optical source, in optical communication with the flow chamber, for providing the beam of electromagnetic radiation; and c) an optical collection system for collecting and directing at least a portion of electromagnetic radiation onto a photodetector; wherein the photodetector produces an electric signal characteristic of the number and/or size of the particles detected; (ii) a fluid monitoring system in fluid communication with the flow chamber that detects bubbles in the liquid, a flow rate condition of the liquid, or both bubbles and a flow rate condition; and (iii) a processor in operational communication with the fluid monitoring system and the optical liquid particle counter, wherein the processor receives monitoring data from the fluid monitoring system and provides a control signal to the optical liquid particle counter or a component thereof resulting in a decrease of the power of the optical source upon detection of bubbles in the fluid or an increase of the power of the optical source upon a period wherein bubbles are not detected the fluid. As used in this context, the expression "a decrease of the power" refers to a change in the power of the optical source resulting in a lower power output of the optical source, including but not limited to decreasing the power output of the optical source to zero (i.e. shutting off the laser) and the expression "an increase of the power" refers to a change in the power of the optical source resulting in a higher power output of the optical source, including but not limited to increasing the power output of the optical from zero to a non-zero value (i.e. turning on the laser).

In an aspect, provided is an optical liquid particle counter system comprising: (i) a liquid particle counter comprising: a) a flow chamber for flowing a liquid containing particles along a flow direction through a beam of electromagnetic radiation, b) an optical source, in optical communication with the flow chamber, for providing the beam of electromagnetic radiation; and c) an optical collection system for collecting and directing at least a portion of electromagnetic radiation onto a photodetector; wherein the photodetector produces an electric signal characteristic of the number and/or size of the particles detected; (ii) a fluid monitoring system in fluid communication with the flow chamber that detects bubbles in the liquid, a flow rate condition of the liquid, or both bubbles and a flow rate condition; (iii) an actuator for engaging or disengaging an optical interrupter capable of redirecting, reshaping, or reducing the amount of electromagnetic radiation from the optical source entering the flow chamber; and (iv) a processor in operational communication with the fluid monitoring system and the actuator, wherein the processor receives monitoring data from the fluid monitoring system and provides a control signal to the actuator for engaging or disengaging the optical interrupter.

As used herein "optical collection system for collecting and directing at least a portion of electromagnetic radiation onto a photodetector" may refer to electromagnetic radiation transmitted through the flow chamber, electromagnetic radiation scattered by particles in the flow chamber, and/or electromagnetic radiation emitted by particles in the flow chamber.

In an embodiment, the control signal is provided by the processor when the processor analyzes the monitoring data and determines the presence of bubbles in the liquid, a flow rate condition of the liquid, or both bubbles and a flow rate condition. In embodiments, for example, the processor flags the monitoring data indicative of the presence of bubbles in the liquid as corresponding to a portion of the liquid in the flow chamber, and the control signal comprises timing instructions for decreasing the power of the optical source or actuating the optical interrupter at a time corresponding to passage of the portion of the liquid through the beam of electromagnetic radiation. In some embodiments, the processor or an additional processor receives the electric signal from the photodetector, and any portion of the electric signal obtained during a period of decreased power of the optical source or a period when the optical interrupter was engaged is excluded or discounted, for example weighted less heavily to other data, during a determination of the number of the particles detected. In some embodiments, the processor receives monitoring data from the fluid monitoring system and provides a control signal to the optical liquid particle counter or a component thereof to increase the power of the optical source to full operational power or to disengage the optical interrupter when the monitoring data indicates the absence of bubbles in the liquid, a normal flow rate condition of the liquid, or both.

In embodiments, during startup of the system, the optical liquid particle counter system will not provide power to the optical source until the processor receives the monitoring data from the fluid monitoring system indicating the absence of bubbles in the liquid, a normal flow rate condition of the liquid, or both. In some embodiments, for example, the full operational power is greater than or equal to 20 mW, 40 mW or, optionally, 100 mW and the normal flow rate is less than or equal to 2000 mL/min, 1000 mL/min or, optionally, 500 mL/min.

In embodiments, particles flow through the beam of electromagnetic radiation, thereby generating scattered or emitted electromagnetic radiation; and the optical collection system collects and directs at least a portion of the scattered or emitted electromagnetic radiation onto the photodetector. In some embodiments, particles flow through the beam of electromagnetic radiation, thereby decreasing transmission of the electromagnetic radiation through the flow chamber; and the optical collection system collects and directs the electromagnetic radiation transmitted through the flow chamber.

Advantageously, the present systems and methods may be used with a wide range of bubble detection systems, including bubble detectors positioned upstream and downstream of the optical liquid particle counter or detection zone of an optical liquid particle counter. In some embodiments, for example, the fluid monitoring system detects bubbles optically, electronically, acoustically, by pressure differential, by density, or a combination thereof. In some embodiments, the processor decreases the power of the optical source if the bubble has a diameter greater than or equal to the diameter of the particles being detected, for example, greater than or equal to 9.8 nm for detection of metals or greater than or equal to 20 nm for polymers, such as polystyrene and latex. In embodiments, the fluid monitoring system comprises an ultrasonic bubble detector, a second optical particle counter, a second optical particle counter with phase monitoring, a capacitive transducer, an optical interrupter, a pressure modulation sensor, a CCD or CMOS camera or a combination thereof. In embodiments, the fluid monitoring system measures quantity, size, density, refractive index, compressibility, fluid capacitance, acoustic properties, or a combination thereof of the bubbles. In some embodiments, for example, the bubbles comprise air, $N_2$, $O_2$, $CO_2$, process gases or a combination thereof.

In some embodiments, the fluid monitoring system is a second optical particle counter with phase monitoring where the particle counter may detect phase modulation in the flow stream and distinguish solid particles from bubbles based on refractive index. An example of an optical particle counter with phase monitoring can be found in US Patent Publication 2015/0260628 and in U.S. Pat. No. 7,746,469, both of which are hereby incorporated by reference in their entirety to the extent not inconsistent herewith.

Recognizing changes in the flow rate of the liquid through the flow chamber is beneficial for both reducing damage to the liquid particle counter and avoiding errors or miscounts due to changes in the way in which particles interact with the optical source at different flow rates. The provided systems and methods may detect a flow stoppage or a flow rate of zero, a low flow rate or a high flow rate with respect to the optimal flow rate or flow rate range for which the particle counter is calibrated. High flow rates are problematic, for example, in negative pressure systems and high flow rates may lead to cavitation of the liquid, thereby causing many of the problems associated with bubbles described herein. In embodiments, the flow rate condition is a high flow rate, a low flow rate, a normal flow rate or a flow stoppage. In embodiments, the flow rate condition corresponds to a normal flow rate and the processor provides a control signal to the optical liquid particle counter or component thereof to increase the power of the optical source. In embodiments, the flow rate condition corresponds to a normal flow rate and the processor provides a control signal actuator to disengage the optical interrupter.

In some embodiments, the fluid monitoring system is a differential pressure flowmeter, a transit-time ultrasonic flowmeter, a rotameter, a float sensor, a Doppler ultrasonic flow meter, a thermal mass flow meter, an electromagnetic flow meter, a turbine/paddle wheel meter, a vortex flow meter, a flow switch, a Coriolis mass flow meter, a CCD or CMOS camera, or a combination thereof. In embodiments, for example, the flow rate condition corresponds to an increase or a decrease of 50% of a normal operating flow rate of the optical liquid particle counter.

Systems and methods provided herein include, in some embodiments, a liquid conditioner which reduces the quantity of bubbles entering the flow chamber of the liquid particle counter. In some embodiments, the systems and methods further comprise a liquid conditioner, wherein the liquid conditioner splits an inlet to the liquid particle counter system into a sampling stream in fluid communication with the flow chamber and a bypass stream and promotes the removal of bubbles out of the sampling stream and into the bypass stream. In embodiments, for example, the sampling stream is positioned gravitationally below the bypass stream. In some embodiments, the liquid conditioner decreases a linear velocity of the liquid within the liquid conditioner with respect to the velocity of the liquid before or after the liquid conditioner. In some embodiments, the liquid conditioner decreases a linear velocity of the liquid within the liquid conditioner with respect to the velocity of the liquid outside of the liquid conditioner by at least 10%, by at least 20% or, optionally, by at least 30%. In an embodiment, the liquid conditioner is a T-junction.

In some cases, it may be advantageous to interrupt the beam of electromagnetic radiation for a brief period corresponding to a flow rate condition or bubbles so that the optical source maintains constant operating power and does not need additional time to reset or repower. In some embodiments, the beam is not fully blocked but partially blocked to allow some electromagnetic radiation to enter the flow chamber, but not enough so as to damage components of the liquid particle counter. In some embodiments, the source continues to provide the normal amount of electromagnetic radiation into the flow chamber, but radiation is interrupted before entering the collection or detection systems.

In embodiments, the optical interrupter is a mirror, an optical filter, a polarization optical switch, a shutter, a beam dump, a beam expanding lens, a heat sink or a combination thereof. In embodiments, the optical interrupter comprises an aperture having an area smaller than a cross section of the beam of electromagnetic radiation. In some embodiments, for example, the optical interrupter reduces a fluence of electromagnetic radiation entering the flow chamber by at least 25%, at least 33% or, optionally, at least 50%.

In an aspect, provided is a method for preventing or minimizing damage to an optical liquid particle counter, the method comprising the steps of: (i) providing a liquid particle counter, the liquid particle counter comprising: a) a flow chamber for flowing a liquid containing particles along a flow direction through a beam of electromagnetic radiation; b) an optical source, in optical communication with the flow chamber, for providing the beam of electromagnetic radiation; and c) an optical collection system for collecting and directing at least a portion of the electromagnetic radiation onto a photodetector; wherein the photodetector produces an electrical signal characteristic of the number and/or size of the particles detected; (ii) detecting bubbles, a flow rate condition, or both bubbles and a flow rate condition in the liquid; and (iii) reducing power supplied to optical source upon detection of the bubbles or the flow rate condition thereby decreasing the power of the beam of electromagnetic radiation, wherein the beam of electromagnetic radiation is characterized as a low power beam of electromagnetic radiation.

In an aspect, provided is a method for preventing or minimizing damage to an optical liquid particle counter, the method comprising the steps of: (i) providing a liquid particle counter, the liquid particle counter comprising: (a) a flow chamber for flowing a liquid containing particles along a flow direction through a beam of electromagnetic radiation; (b) an optical source, in optical communication with the flow chamber, for providing the beam of electromagnetic radiation; and (c) an optical collection system for collecting and directing at least a portion of the electromagnetic radiation onto a photodetector; wherein the photodetector produces an electric signal characteristic of the number and/or size of the particles detected; (ii) detecting bubbles, a flow rate condition, or both bubbles and a flow rate condition in the liquid; and (iii) interrupting the beam by preventing at least a portion of the electromagnetic radiation from the optical source from entering the flow chamber upon detection of bubbles, a flow rate condition, or both bubbles and a flow rate condition in the liquid.

In an aspect, provided is an optical liquid particle counter system comprising: (i) a liquid particle counter comprising: a) a flow chamber for flowing a liquid containing particles along a flow direction through a beam of electromagnetic radiation, thereby generating scattered or emitted electromagnetic radiation from the particles in the liquid; b) an optical source, in optical communication with the flow chamber, for providing the beam of electromagnetic radiation; and c) an optical collection system for collecting and directing at least a portion of the scattered or emitted electromagnetic radiation from the particles onto a photodetector; wherein the photodetector produces an electric signal characteristic of the number and/or size of the particles detected; and (ii) a bubble detector in fluid communication with the flow chamber and the optical source for detecting bubbles in the liquid.

In an embodiment, the optical liquid particle further comprises a processor in operational communication with the fluid monitoring system and the optical liquid particle counter, wherein the processor receives monitoring data from the bubble detector and provides a control signal to the optical liquid particle counter or a component thereof to decrease the power of the optical source, thereby powering off the optical source. In an embodiment, the bubble detector characterizes the bubbles in the liquid, for example, by determining the quantity, size, density, refractive index, compressibility, fluid capacitance, acoustic properties, or a combination thereof of the bubbles in the liquid. In some embodiments, the system further comprises a processor in operational communication with the bubble detector and the optical liquid particle counter, wherein the processor analyzes a signal corresponding to the bubbles provided by the bubble detector and characterizes the bubbles and the processor adjusts and operating parameter or output of the liquid particle counter based on the bubble characterization.

In embodiments, the bubble detector is positioned upstream or downstream of the liquid particle counter.

In an aspect, provided herein is an optical liquid particle counter system comprising: (i) a liquid particle counter comprising: a) a flow chamber for flowing a liquid containing particles along a flow direction through a beam of electromagnetic radiation, b) an optical source, in optical communication with the flow chamber, for providing the beam of electromagnetic radiation; and c) an optical collection system for collecting and directing at least a portion of electromagnetic radiation onto a photodetector; wherein the photodetector produces an electric signal characteristic of the number and/or size of the particles detected; (ii) a flow rate monitoring system in fluid communication with the flow chamber that monitors a liquid flow rate; and (iii) a processor in operational communication with the flow rate monitoring system and the photodetector, wherein the processor adjusts an operating parameter or output of the liquid particle counter based on the liquid flow rate.

In embodiments, for example, the operating parameter is a threshold value of the electromagnetic radiation that corresponds to a particle. In some embodiments, the operating parameter is power provided to the optical source, wherein the power is increased or decreased so that the photodetector produces the same electric signal corresponding to a particle independent of flow rate. In embodiments, the output is total volume analyzed by the liquid particle counter. In some embodiments, the particles flow through the beam of electromagnetic radiation, thereby generating scattered or emitted electromagnetic radiation; and the optical collection system collects and directs at least a portion of the scattered or emitted electromagnetic radiation onto the photodetector. In some embodiments, particles flow through the beam of electromagnetic radiation, thereby obscuring at least a portion of the electromagnetic radiation; and the optical collection system collects and directs the electromagnetic radiation that has not been obscured onto the photodetector. In embodiments, for example, the flow rate condition is a high flow rate, a low flow rate, a normal flow rate or a flow stoppage.

In an aspect, for example, the invention provides an optical liquid particle counter system comprising: (i) a liquid particle counter comprising: (1) a flow chamber for flowing a liquid containing particles along a flow direction through a beam of electromagnetic radiation, (2) an optical source, in optical communication with the flow chamber, for providing the beam of electromagnetic radiation; and (3) an optical collection system for collecting and directing at least a portion of electromagnetic radiation onto a photodetector; wherein the photodetector produces an electric signal characteristic of the number and/or size of the particles detected; (ii) a fluid monitoring system in fluid communication with the flow chamber; and (iii) a processor in operational communication with the fluid monitoring system to receive monitoring data from the fluid monitoring system; wherein the processor analyzes the monitoring data to determine a state of the optical liquid particle counter system corresponding to a normal operation state or a non-normal operation state. In an embodiment, the processor determines states of the optical liquid particle counter system as a function of time, for example, determining successive states of the optical liquid particle counter system. In an embodiment, for example, changes in the states as a function of time provides an input for control of the optical liquid particle counter system. In an embodiment, for example, changes in the states as a function of time provides an input for or the analysis of the electric signals from the photodetector to determine the number and/or size of particles in the liquid.

In an embodiment of this aspect, upon the determination of a normal operating state subsequent to a determination of a non-normal operating state, the system transitions from a non-normal operating mode to a normal operating mode. In an embodiment, for example, the transition from the non-normal operating mode to the normal operating mode occurs on a first timescale, such as a first timescale equal to or greater than 15 seconds, greater than or equal to 30 seconds, or optionally greater than or equal to 60 seconds. In embodiments, the first time scale is selected form the range of 1 to 15 seconds, 1 to 30 seconds, or optionally, 1 to 60 seconds. In an embodiment, for example, the normal operating mode corresponds to one or more of the criteria selected from the group consisting of: no bubbles detected in the liquid, no detection of a flow stoppage of the liquid, no detection of a change in flow rate greater than a preselected value and no detected leaks.

In an embodiment, for example, upon the determination of a non-normal operating state subsequent to a determination of a normal operating state, the system transitions from a normal operating mode to a non-normal operating mode. In an embodiment, for example, the transition from the normal operating mode to the non-normal operating mode occurs on a second timescale, such as a second timescale equal to or less than 2 seconds, less than or equal to 5 second, less than or equal to 10 seconds, or, optionally, less than or equal to 15 seconds. In embodiments, the second time scale is selected form the range of 1 to 2 seconds, 1 to 1 seconds, or optionally, 1 to 15 seconds. In an embodiment, for example, the non-normal operating state the system corresponds to one or more criteria selected from the group consisting of: detection of one or more bubbles in the liquid, detection of a flow stoppage, and detection of a change in flow rate greater than a preselected value. In an embodiment, for example, the monitoring data from the fluid monitoring systems is provided in a buffer, wherein detection of one or more bubbles in the liquid is achieve by evaluating the monitoring data in buffer to identify one or more conditions selected from the group consisting of: a number of contiguous dry elements, a total number of dry elements and a ratio of dry elements to wet elements. In an embodiment, for example, upon determination of the non-normal operating state, the system flags liquid particle counter data from the photodetector for a period of time at least until the processor determines one or more subsequent states of the optical liquid particle counter system corresponding to a normal operation state. In an embodiment, for example, upon determination of the non-normal operating state, the system modulates at least one property of the optical source or beam of radiation for a period of time at least until the processor determines one or more subsequent states of the optical liquid particle counter system corresponding to a normal operation state, such as at least one property of the optical source or beam of radiation selected from the group consisting of the power, intensity, fluence and spatially intensity distribution of the beam of radiation.

In an aspect, provided is an optical liquid particle counter system comprising: (i) a liquid particle counter comprising: a) a flow chamber for flowing a liquid containing particles along a flow direction through a beam of electromagnetic radiation, b) an optical source, in optical communication with the flow chamber, for providing the beam of electromagnetic radiation; and c) an optical collection system for collecting and directing at least a portion of electromagnetic radiation onto a photodetector; wherein the photodetector produces an electric signal characteristic of the number and/or size of the particles detected; (ii) a fluid monitoring system in fluid communication with the flow chamber that detects bubbles in the liquid, a flow rate condition of the liquid, or both bubbles and a flow rate condition; and (iii) a processor in operational communication with the fluid monitoring system and the optical liquid particle counter, wherein the processor determines a non-normal operating state and the system flags liquid particle counter data from the photodetector for a period of time at least until the processor determines one or more subsequent states of the optical liquid particle counter system corresponding to a normal operation state.

DETAILED DESCRIPTION OF THE INVENTION

Figure 1:
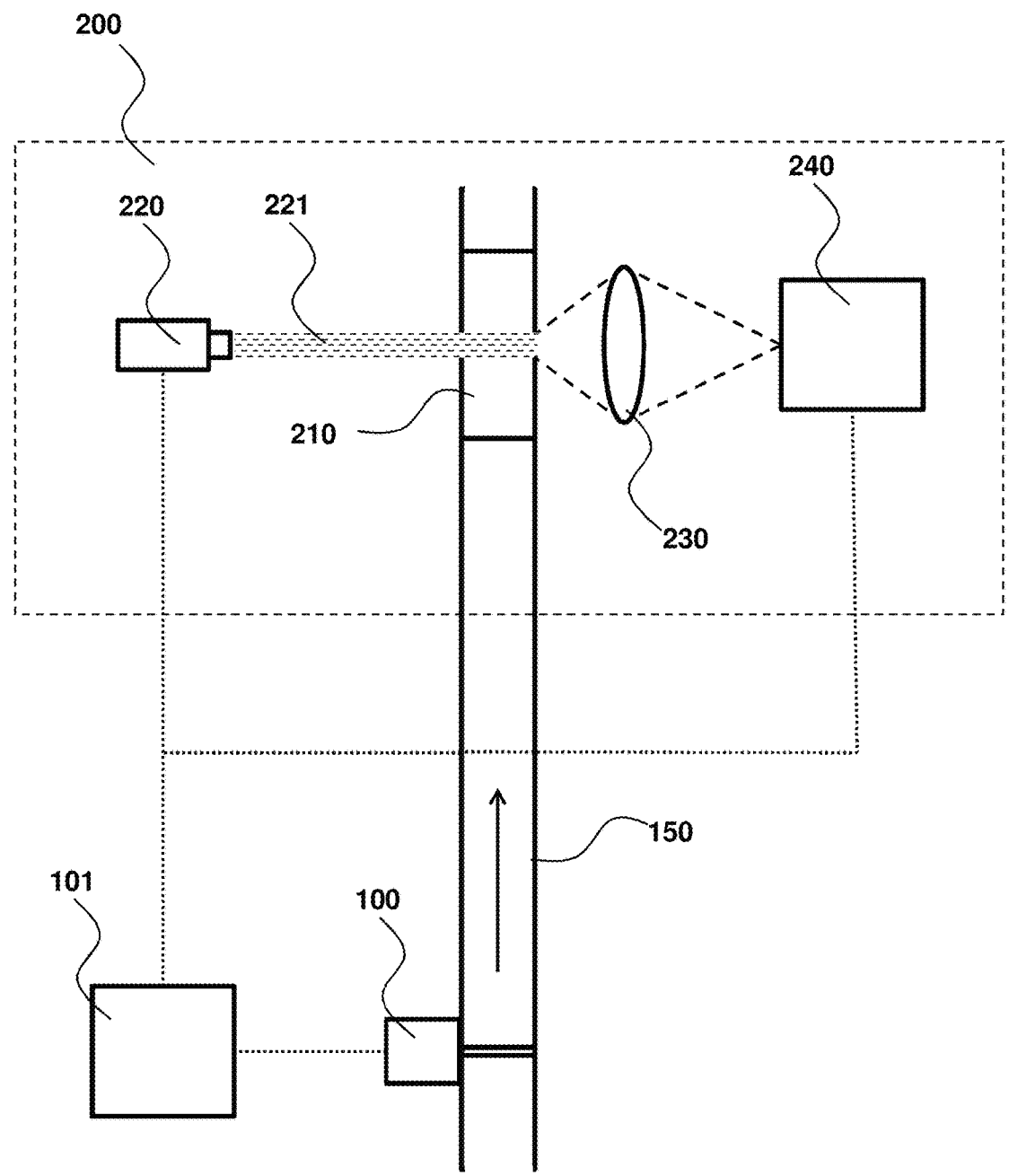
FIG. 1. Provides a schematic of an integrated Automatic Power Control (APC) fluid monitoring system and liquid particle counter.

In general the terms and phrases used herein have their art-recognized meaning, which can be found by reference to standard texts, journal references and contexts known to those skilled in the art. The following definitions are provided to clarify their specific use in the context of the invention.

"Fluid monitoring system" refers to a device or series of devices for measuring fluid properties, for example, devices or sensors which detect bubbles, measure flow rate or both. In embodiments, for example, fluid monitoring system refers to an optical, electronic, acoustic, or pressure sensor. In some embodiments, fluid monitoring system refers to an ultrasonic bubble detector, a second optical particle counter, a capacitive transducer, an optical interrupter, a pressure modulation sensor, a CCD or CMOS camera, a differential pressure flowmeter, a transit-time ultrasonic flowmeter, a rotameter/float sensor, a Doppler ultrasonic flow meter, a thermal mass flow meter, an electromagnetic flow meter, a turbine/paddle wheel meter, vortex flow meter, a flow switch, a Coriolis mass flow meter, or a combination thereof. In embodiments, the flow monitoring system is positioned upstream from the liquid particle counter. The flow monitoring system may be positioned a distance from the liquid particle counter based on the flow rate of the system, to allow for sufficient time for processing of the signal flow monitoring system and control of the optical source (e.g. reduction in power, engagement of an interrupter, power off).

"Optical interrupter" refers to a device which inhibits the fluence of electromagnetic radiation. In some embodiments, the optical interrupter inhibits electromagnetic radiation from entering the flow chamber, the collection system, the detection system, or a combination thereof, of the liquid particle counter. In some embodiments, the interrupter deflects, absorbs, diffuses, obscures, redirects or blocks electromagnetic radiation. In embodiments, for example, the optical interrupter is a mirror, an optical filter, an optical mask, a polarization optical switch, a shutter, a beam dump, a beam expanding lens, a heat sink, an aperture or a combination thereof.

"Flow rate condition" refers one or more parameters associated with a moving fluid, such as the rate of the fluid movement, volume of the moving fluid, change in rate over distance or time, change in volume over distance or time, or a combination thereof. In some embodiments, flow rate condition refers to a stoppage of flow. In some embodiments, flow rate condition refers to a change in flow rate, for example, a change in flow rate of greater than 10%, 25%, or optionally, 50%. In embodiments, flow rate condition refers to a change in type of flow rate (e.g. a normal flow rate, a low flow rate, a flow stoppage or a high flow rate) to another type of flow rate. In some embodiments, for example, a flow rate condition is a difference in flow rate of greater than or equal to 25%, 33% or 50% of the optimal flow rate of the liquid particle counter. In some embodiments, flow rate condition refers to a normal flow rate, an optimal flow rate or a flow rate favorable for counting particles.

"Liquid conditioner" refers to a device which separates a flow into at least two streams, in which bubbles are more likely to enter one stream than another. In an embodiment, for example, a liquid conditioner is a T-junction which reduces the linear velocity of the liquid flowing through the conditioner and bubbles within the liquid flow tend to rise to the top of the junction and enter the upward flowing stream due to buoyancy, while the downward flowing stream is less likely to contain bubbles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Optical communication" refers to components which are arranged in a manner that allows light or electromagnetic radiation to transfer between the components.

"Optical source" refers to a device or device component that is capable of delivering electromagnetic radiation to a sample. The term is not limited to visible radiation, such as by a visible light beam, but is used in a broad sense to include any electromagnetic radiation. The optical source may be embodied as a laser or laser array, such as a diode laser, diode laser array, diode laser pumped solid state laser, LED, LED array, gas phase laser, solid state laser, or combinations thereof.

The term "electromagnetic radiation" and "light" are used synonymously in the present description and refer to waves of electric and magnetic fields. Electromagnetic radiation useful for the methods of the present invention includes, but is not limited to ultraviolet light, visible light, infrared light, or any combination of these having wavelengths between about 100 nanometers (nm) to about 15 microns (µm).

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these.

"Particles" refers to small objects which are often regarded as contaminants. A particle can be any material created by the act of friction, for example when two surfaces come Into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 µm. A particle may refer to any small object which absorbs or scatters light and is thus detectable by an optical particle counter. As used herein, "particle" is intended to be exclusive of the individual atoms or molecules of a carrier fluid, for example water molecules, process chemical molecules, oxygen molecules, helium atoms, nitrogen molecules, etc. Some embodiments of the present invention are capable of detecting, sizing, and/or counting particles comprising aggregates of material having a size greater than 10 nm, 20 nm, 30 nm, 50 nm, 100 nm, 500 nm, 1 µm or greater, or 10 µm or greater. Specific particles include particles having a size selected from 20 nm to 50 nm, 50 nm to 50 µm, a size selected from 100 nm to 10 µm, or a size selected from 500 nm to 5 µm.

The terms "optical liquid particle counter" and "particle counter" are used interchangeably herein and refer to systems capable of detecting particles suspended in a liquid, systems capable of determining the sizes of particles suspended in a liquid, systems capable of counting particles suspended in a liquid, systems capable of classification of particles suspended in a liquid, or any combination of these. A typical optical liquid particle counter is comprised of several components, such as a source for generating a beam of electromagnetic radiation, optics for directing the beam into a region where a fluid sample is flowing, for example a liquid or gas flowing through a flow cell. A typical optical liquid particle counter is also comprised of a photodetector, such as a two-dimensional optical detector, and collection optics for detecting electromagnetic radiation which is obscured, scattered or emitted by particles which pass through the beam, and other electronics for the processing and analysis of electrical signals produced by the photodetector including current to voltage converters and signal filtering and amplification electronics. An optical particle counter may also be comprised of a pump for creating a flow for introducing a liquid sample to the detection region where the electromagnetic beam is present.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through a detection zone of a liquid particle counter. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area.

The invention is further detailed in the following Examples, which are offered by way of illustration and are not intended to limit the scope of the invention in any manner.

Example 1—Fluid Monitoring System with Optical Source Power Reduction and Data Adjustment Certain conventional liquid particle counters are susceptible to problems arising from changes in flow rate and/or the presence of bubbles in the liquid being analyzed. In some circumstances, for instance, optical scattering from bubbles may be indistinguishable from that arising from solid particles and are, thus, counted as contaminants resulting in false positive counts. Further, in high power particle counters, bubbles may refract a large amount of radiation, thereby causing significant scattering or redirection of the beam, resulting in damage to internal components, including the source (e.g. laser) itself. Changes in flow rates may cause similar problems, as low flow rates are susceptible to conditions wherein the fluid sample may undergo an undesired phase change (e.g. boiling) in the flow cell, thus creating bubbles, or overheating and thermally damaging components of the particle counter. Sampling liquids contaminated with larger particles can create flow cell damage by burning viewing windows inside the flow cell if these large particles become stationary in the high radiation field when flow is reduced of stopped. Liquid particle counters are also typically calibrated for a specific flow rate and, therefore, changes in flow rate may impact the ability of the particle counter to accurately characterize the particle, e.g. with respect to size. Further, high flow rates may cause cavitation, creating pockets of air or bubbles and similar challenges in negative pressure systems.

An approach to address these problems is to implement monitoring of the liquid under analysis, for example, to measure the presence of bubbles and/or changes in flow rate. This information is used to control operation of the particle counter and/or optimize the analysis of particle counting data. In an embodiment, measurements of flow rate parameters and/or identification of bubbles in a liquid is used as the basis for adjusting operating conditions, such as properties of the optical source (e.g. power, intensity, fluence), for example, when bubbles are transported through the flow chamber or when the flow rate is outside of operational parameters. Further, monitoring the fluid for bubbles and changes in flow rate enables approaches to adjust data analysis to quantitatively take into consideration bubbles (e.g., by removing those data points from final counts) and/or changes in flow rates (e.g. by adjusting detection parameters). After operational periods corresponding to bubbles or a non-optimal flow rate have passed, for example, the systems may be returned to a normal operating condition quickly in order to ensure the maximum extent of liquid is analyzed by the particle counter.

An integrated fluid monitoring system and liquid particle counter is provided in FIG. 1. A fluid monitoring system 100 comprising, for example, an ultrasonic bubble detector and a flow meter, is configured to analyze a liquid flowing through a conduit 150 for passing a liquid sample under analysis. A liquid particle counter 200 is provided in fluid communication with the liquid conduit 150 so that the liquid flows through the flow chamber 210 of the particle counter. An optical source 220, such as a laser or light emitting diode, generates a beam of electromagnetic radiation 221 that is passed through the flow chamber 210 such that the beam interacts with particles as they flow through the flow chamber 210. Transmitted, scattered or emitted electromagnetic radiation is collected by a collection system 230 and directed onto a detector system 240 which generates electrical signals corresponding to particles or characteristics of the particles passing through the flow cell.

Figure 6:
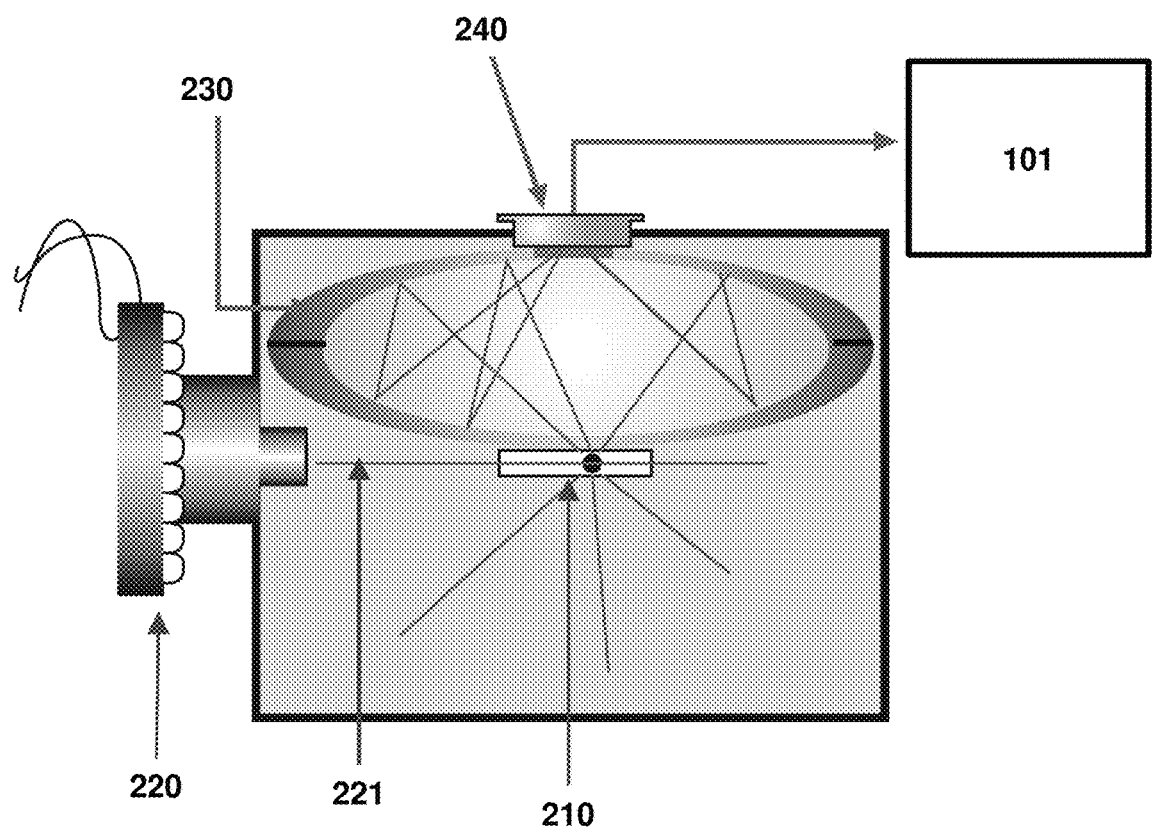
FIG. 6. Shows a top view of a liquid particle counter configured to collect scattered light at a 90° angle from the optical source.

FIG. 1 provides a schematic diagram illustrating an obscuring or eliminating liquid particle counter. The concepts and embodiments described herein, however, are also applicable to other types of particles counters including scattered light or emitted light particle counters. FIG. 6 illustrates, for example, a configuration of a scattering liquid particle counter, wherein the detection system is offset (e.g., by 90°) from the path of the electromagnetic radiation 221 from the optical source 220. FIG. 6 provides a top view of the liquid particle counter, and the flow direction is orthogonal to the plane being viewed. Given this perspective, the fluid monitoring system, provided either upstream or downstream from the flow chamber 210, is not shown in FIG. 6.

A shown in FIG. 1, the fluid monitoring system 100 is provided in data communication with a processor 101, for example, such that fluid monitoring system 100 provides signals to the processor 101, for example, upon detection of a bubble and/or a change in flow rate through the flow cell 210, including a flow stoppage. In some embodiments, the processor 101 is in one way or two way data communication with the optical source 220 and in one way or two way data communication the detection system 240 (as illustrated by the dotted lines in FIG. 1). Arrows indicate flow direction. In an embodiment, for example, processor 101 is configured to send signals to optical source 220 and configured to receive signals from detection system 240.

In an embodiment, the fluid monitoring system 100 is a flow monitoring system, such as a rotameter having a flow range of 10 cm$^3$/min-75 cm$^3$/min, a low flow indication of 5 cm$^3$/min (with decreasing flow), a good flow indication of 5 cm$^3$/min (with selectable Hysteresis), a fluid temperature range of 15° C.-50° C., a fluid pressure range of 20 psi-60 psi and/or is compatible with water and/or semiconductor processing chemicals. In an embodiment, the fluid monitoring system 100 is an ultrasonic bubble detector having a minimum bubble detection size of 1 μm (selectable), detection indications including fluid, air, TTL high and TTL low and/or a response time of 50 μs.

Upon receiving a signal(s) corresponding to the detection of a bubble or a change in flow rate condition from the fluid monitoring system 100, the processor 101 may initiate several actions to control operating conditions and/or adjust data analysis. In the event of detection of a bubble or detection of a change in flow rate, for example, the processor 101 may decrease the power provided to the optical source 220, thereby reducing the intensity, fluence and/or power of electromagnetic radiation 221 provided to the flow chamber 210. Such functionality may be useful for reducing the risk of damage to the components of the liquid particle counter 200. In embodiments, for example, the power is reduced to safe levels while continuing to provide electromagnetic radiation 221 to the flow cell 210, for example ≤50% in reference to normal operation, in order to avoid cessation of electromagnetic radiation and/or restarting the optical source 220.

In some embodiments, upon receiving a signal from fluid monitoring system 100, the processor 101 may flag as not being associated with solid particles the electric signals provided by the detection system 240 during the period corresponding to a condition wherein bubbles are in the flow cell 210. In some embodiments, for example, the flagged signals may be disregarded as not being associated with solid particles. In some embodiments, upon receiving a signal from fluid monitoring system 100, the processor 101 increases the power of the optical source 220 and analyzes signals provided by the detection system 240 normally, once the absence of bubbles has been detected by the fluid monitoring system 100. Optionally, the processor 101 may provide a control signal(s) to reduce the power of the optical source 220 power and/or flag particle counter data obtained during a change in flow rate. Optionally, the processor 101 may increase the power of the optical source 220 and analyze signals provided by the detection system 240 normally, once a normal flow rate has been detected by the fluid monitoring system 100.

Additionally, the fluid monitoring system 100 may be configured to provide flow rate data to the processor 101 for the purpose of adjusting, such as optimizing, the analysis of particle detection signals from detection system 240. In an embodiment, for example, the processor 101 selected or adjusts detection and characterization parameters, such as intensity thresholds used to detect and characterize particulates, to address for the impact of changes in flow rate on the analysis of optical particle counter data. Alternatively, the processor 101 may address the impact of changes in flow rate on the analysis of optical particle counter data by increase or decrease the power provided to the optical source 220, and hence the intensity, fluence and/or power of electromagnetic radiation provided to the flow cell. This approach may be useful for embodiments wherein threshold intensities are kept constant and changes in flow rate are addressed via modulation of the intensity, fluence and/or power of electromagnetic radiation provided to the flow cell.

In some embodiments, the measured flow rate enables the detection system 240 to directly measure the amount of liquid analyzed over time, in contrast to assuming a constant flow, thereby providing more accurate particle per volume information.

Example 2—Fluid Monitoring System with Optical Source Interruption and Data Adjustment Another solution to the safety and data integrity issues in optical liquid particle counters caused by bubbles or changes in flow rate (e.g. damage to components, data integrity issues) may be achieved by interrupting or otherwise modulating the optical source, thereby minimizing degradation or damage of the collection and detection systems upon conditions corresponding to bubbles and/or a change in flow rate.

Figure 2:
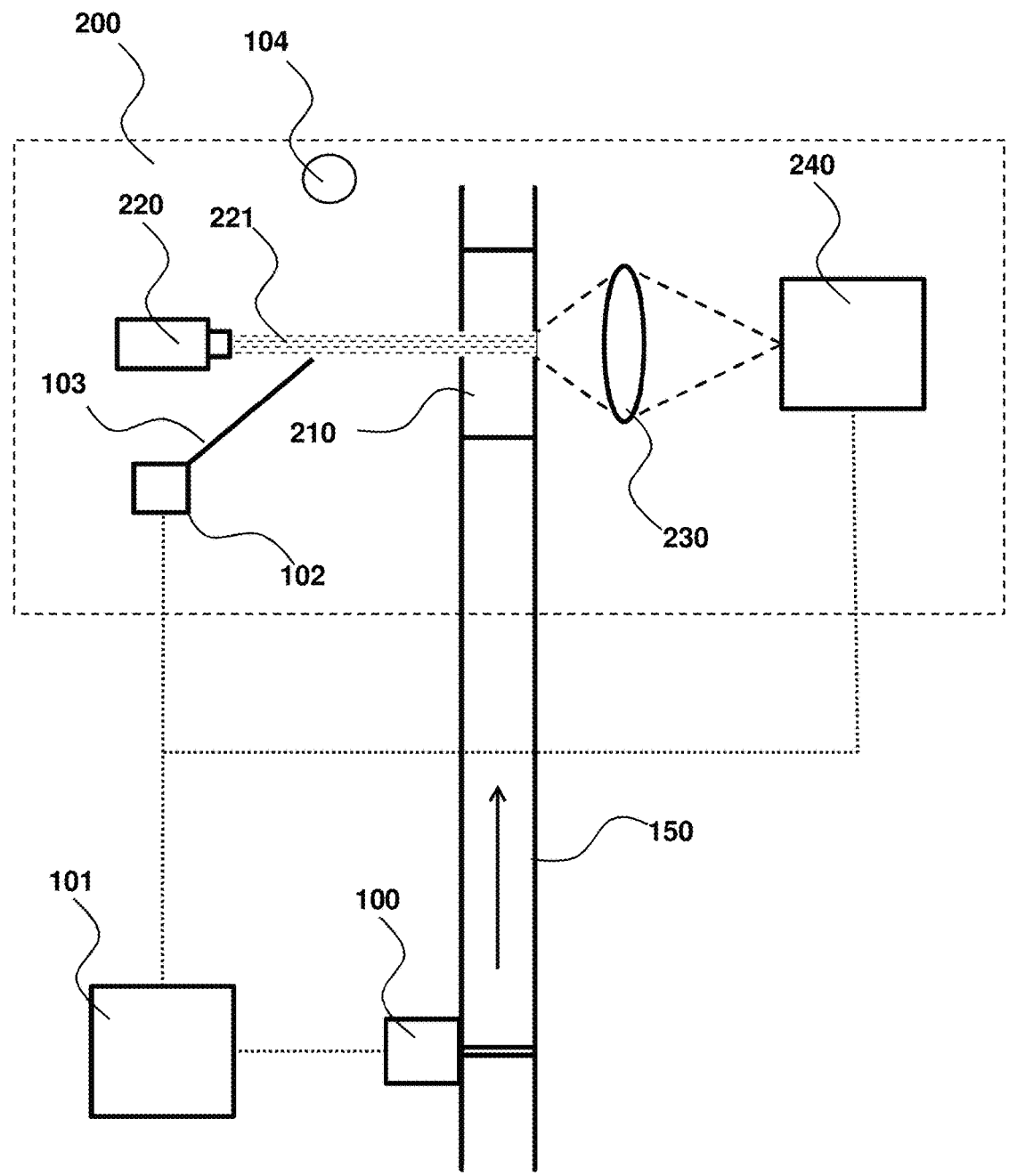
FIG. 2. Provides a schematic of an integrated interrupter-based fluid monitoring system and liquid particle counter during normal (uninterrupted) operation.
Figure 3:
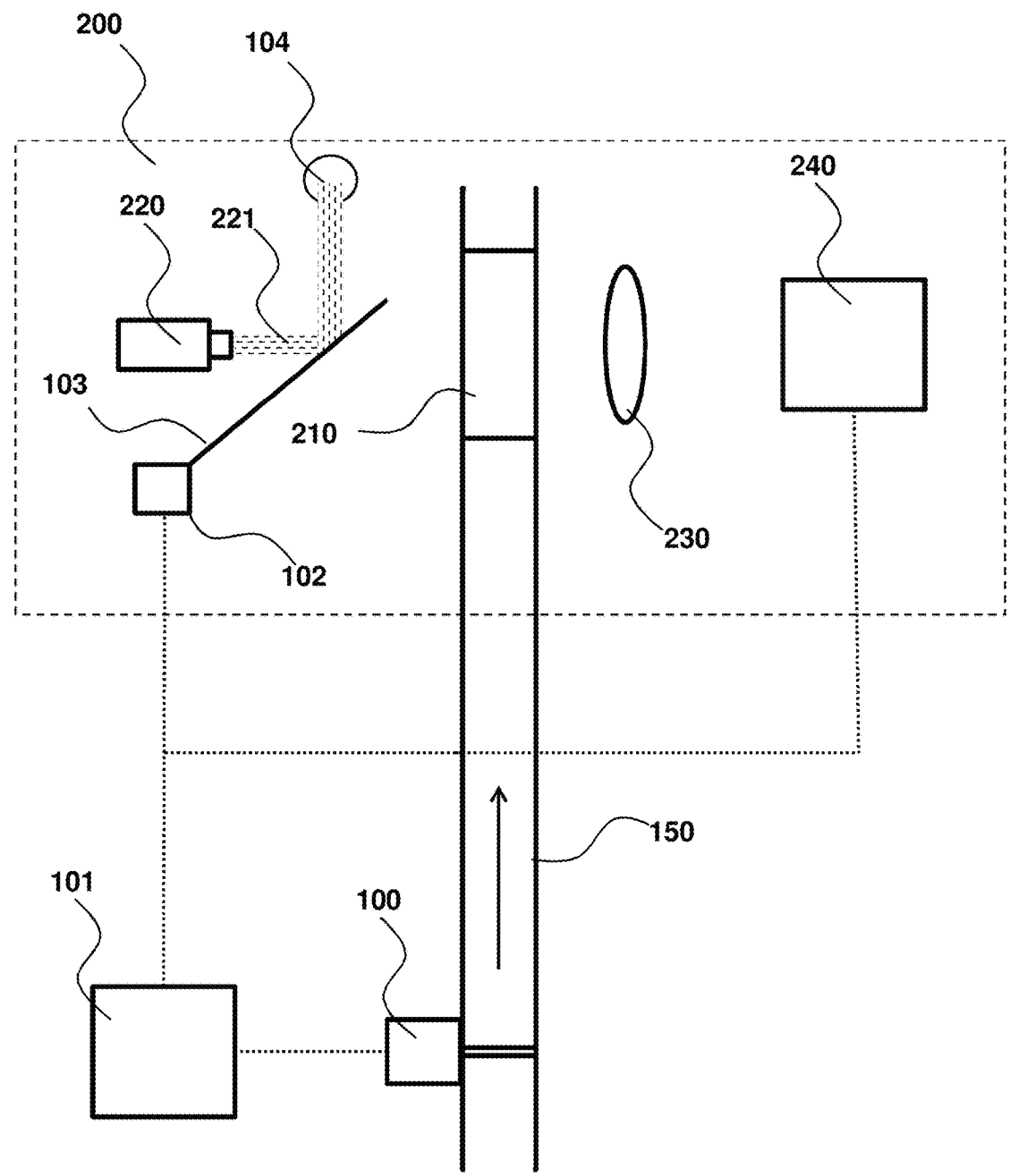
FIG. 3. Provides a schematic of an integrated interrupter-based fluid monitoring system and liquid particle counter with the interrupter engaged.

An example of an interrupting fluid monitoring system is described in FIGS. 2 and 3. The concepts and embodiments described herein, however, are also applicable to other types of particles counters including scattered light or emitted light particle counters as illustrated in FIG. 6.

In an embodiment, when the fluid monitoring system 100 detects either a bubble or a change in flow rate, including a flow stoppage, it provides a signal(s) to the processor 101. As shown in FIG. 6, the processor 101 is in one or two way data communication with an actuator 102 and/or the detection system 240. The actuator 102 is configured to engage an optical interrupter 103, for example, a mirror, filter, diffuser or optical mask, upon detection of bubbles or a change in flow rate. FIG. 2 illustrates the system during normal operation. FIG. 3 shows the system with the optical interrupter 103 engaged to prevent at least some of the electromagnetic radiation 221 from entering the flow chamber 210, and instead directs the radiation to a laser beam dump 104 or otherwise modulates the intensity and/or spatially characteristics of the beam. Arrows indicate flow direction. Optical interrupters useful in this aspect of the invention include an optical mask, a reflector, a lens, a diffuser, a filter, an aperture or a shutter, or a combination thereof. The processor 101 may flag, or in some embodiments disregard, the electrical signal provided by the detection system 240 for periods in which the optical interrupter 103 is engaged. In some embodiments, the optical interrupter may be placed instead between the flow chamber 210 and the collection system 230, allowing the electromagnetic radiation 221 to enter the flow chamber 210 but not to reach the detection system 240. Advantageously, this allows the optical source 220 to continue to operate as normal, avoiding problems resulting in restarting or repowering the source 220. Once the fluid monitoring system 100 has detected that bubbles are no longer present and/or the flow rate is a normal flow rate condition, the processor 101 may provide a signal(s) to the actuator 102 to disengage the optical interrupter 103, so as to allow the optical particle counter to return to normal operation.

Additionally, if the flow rate changes but does not represent a danger to the internal components, the optical interrupter 103 may be left disengaged and the fluid monitoring system 100 may provide a signal to the processor 101 corresponding to the measured flow rate. In some embodiments, for example, the processor 101 adjusts the detection and characterization parameters, for example, intensity thresholds used to detect and characterize particles, thereby continuing to accurately monitor and collect data even during changes in flow rate. The processor 101 may also, in some embodiments, increase or decrease the power provided to the optical source 220, thereby keeping threshold intensities constant but addressing the presence of bubbles or changes in flow rate by adjusting the output of the optical source.

Example 3—Fluid Conditioner

In addition to the protective measures and optimizing the analysis of particle counter data on the basis of the detection of bubbles and changes in flow rate, it is also advantageous in some embodiments to control and/or reduce the amount of bubbles that may enter the system. Bubbles entering the flow chamber may be controlled, for example, by including a liquid conditioner upstream from the particle counter, to reduce the number or size of bubbles in the fluid being analyzed. In an embodiment, for example, the liquid conditioner may split the liquid stream being analyzed into two separate streams, with one stream having a larger concentration of bubbles.

Figure 4:
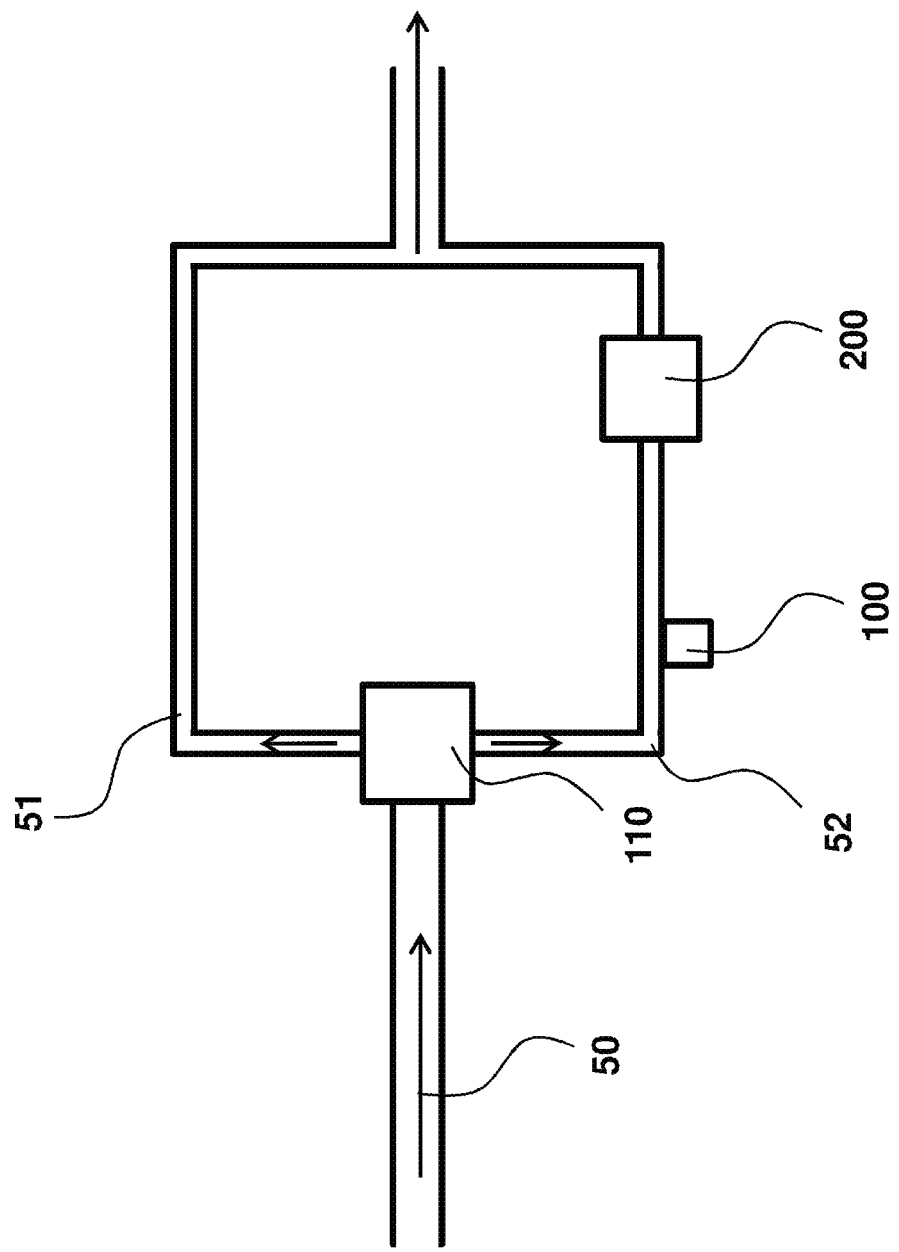
FIG. 4. Provides a schematic of an integrated fluid monitoring system and liquid particle counter with a liquid conditioner to reduce the occurrence of bubbles.
Figure 5:
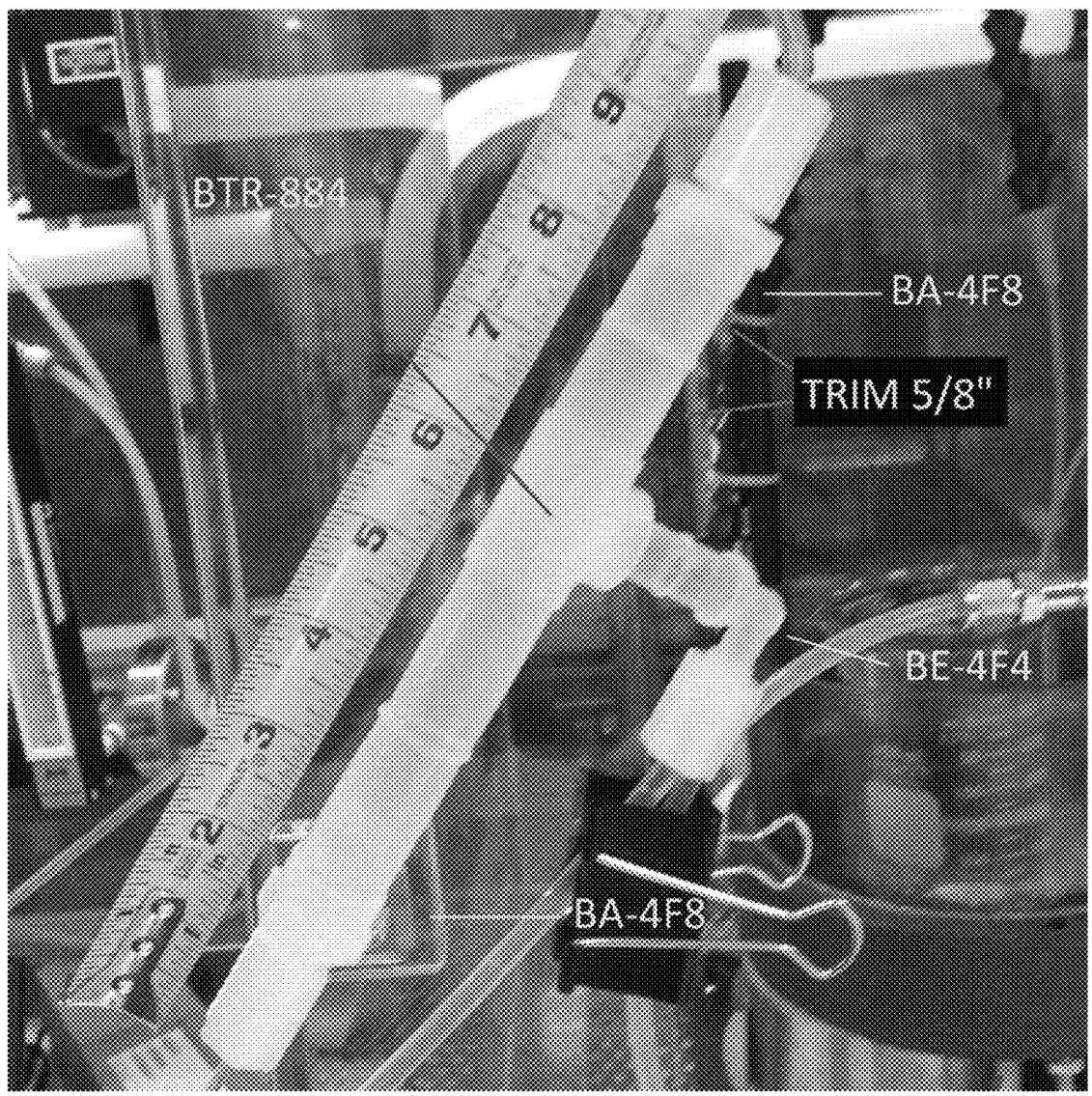
FIG. 5. Shows an example of a liquid conditioner.

FIG. 4 provides a schematic of a system utilizing a liquid conditioner and FIG. 5 shows an exemplary liquid conditioning device. In FIG. 4, the liquid stream 50 being analyzed is split into two separate streams, a bypass stream 51 and a sample stream 52 after passing through the liquid conditioner 110. The liquid conditioner 110 decreases the linear velocity of the fluid allowing bubbles to rise to the top of the stream due to their lower density. Thus, bubbles are more likely to enter the bypass stream 51 which is positioned gravitationally above the sample stream 52. In this configuration, the liquid which enters the sample stream will contain fewer bubbles as it passes through the fluid monitoring system 100 and the liquid particle counter 200. Accordingly, this configuration is beneficial for suppressing problems arising from the presence of bubbles, such as the occurrence of false positives.

Example 4—Integrated System

Particle counters integrating fluid monitoring as provided herein achieves certain benefits over conventional systems.

Damage: High laser energy density can cause potential for instrument damage in the event fluid flow is insufficient to avoid overheating or boiling within the sample cell. Identification of flow reduction or stoppage can allow laser energy to be terminated, diminished or redirected until appropriate flow rates are regained.

Gas bubbles passing through the measurement region of the sample cell will scatter light similarly to a particle. Since optical particle counters measure scattered light, they rely on index of refraction variances between the media and particles to cause light scattering. A gas bubble having an index of refraction different from the sample media will scatter light in the same manner as a particle. If the gas bubble is sufficiently large, it can scatter and redirect sufficient laser energy to cause damage to sensitive components inside the particle counter. These components could include the laser itself, sample cell components and photodetectors or other electronics.

Data Quality: Additional advantages may be gained while monitoring flow rates and adjusting operational parameters to compensate data for flow fluctuations. In the case of bubbles, identification of bubble activity would support elimination of those data from the reported measurements or support flagging the data as being of questionable accuracy. The benefits of both these capabilities are improved data quality and reliability.

Sample conditioning: In addition to bubble detection, integration of an apparatus to separate bubbles from the fluid flow being analyzed by the optical particle counter improves data quality. Conditioning devices can be, for example, a vessel allowing bubbles to rise due to buoyancy while the sample flow is taken from the bottom of the vessel. The portion of the flow with bubbles would bypass the sample region and thereby not impact data quality. Other apparatus using permeation membranes, tubes or other degassing mechanisms could be used. An example of one embodiment is provided in FIG. 5.

Example 5—Fluid Monitoring System Switching

In some embodiments, the fluid monitoring system provides control signal(s) to the liquid particle counter to rapidly switch between normal operation and an altered safety state where the power to the laser is changed, an optical interrupter is engaged, or output data is flagged, or in some embodiments disregarded, in order to improve data integrity. This allows for control of the liquid particle counter in real time and avoidance of damage and inaccurate data analysis while automatically returning to normal operation when bubbles have passed or the flow rate has returned to a normal flow rate condition. Each switch type can be individually enabled or disabled.

In an embodiment, for example, the processor includes logic to switch a condition in the liquid particle counter or flag data provided by the optical detection system upon receiving a signal from the fluid monitoring system corresponding to the presence of bubbles or a change in flow rate condition. The processor analyzes a switch "Reading" and a switch "State" to determine when to provide a control signal to the liquid particle counter. A Reading depends on the amount of time/criteria to tell if the switch input is determined to be definitely one condition (e.g. the presence of bubbles or a low flow rate condition). A State depends on the amount of time/criteria to tell whether or not the switch input is determined to be Bad or Good.

In some embodiments, the Bad state is what initiates the optical source protection processing, for example, initiating the optical interrupter or reducing laser power and flagging corresponding to the Bad state. A Good state will return the optical source to its normal runtime configuration. The unit will only set the optical source to its normal runtime configuration if after boot a good startup value is determined from each enabled switch (e.g. the absence of bubbles or a normal flow condition, and in some embodiments, both) The reading time/criteria is the same for the transition between either of the two possibilities for each switch type. The transition time/criteria from Good-to-Bad State may be different from the transition from Bad-to-Good state. The transition between readings utilizes a time/criteria which minimizes the possibility of false indications The criteria for the bubble detector may include other parameters in addition to timing:
Take a wet/dry reading at a rate that is relatively high as compared to the nominal system flow rate (e.g. 1 mSec)
Maintain a circular buffer of wet/dry readings (e.g. 100 elements)
Process entire buffer every time it is loaded:
Fail if number of contiguous dry elements>X
Fail if number of total dry elements>Y
Fail if number of dry/wet>N/M There are additional "patterns" that can be implemented as buffer size is increased. In some embodiments, more complex patterns may be analyzed to determine the presence of bubbles.

Example 6—System Control

Optical Source (Laser) Controller

A laser controller in the instrument's firmware may be used for setting the desired laser power. For example, it can poll the laser module for its measured laser power, its temperature reading and processes any requested laser on/off commands.

The laser controller may also request the status of any/all of the Fluid Check switches that are enabled. If any/all of the switches that are enabled have triggered (i.e., bad switch status) then the laser is automatically shut-off. At initialization, the laser controller waits until all enabled fluid monitoring systems (or fluid check switches) have a determined good state before turning the laser on. Fluid monitoring systems include but are not limited to Bubble detector and Flow indicator.

An example mode of the laser controller is Auto: When the fluid check switch status goes from bad to good—the laser will be automatically powered on and when the fluid check switch status goes from good to bad—the laser will be automatically powered off.

Fluid Monitoring/Fluid Check Processing

The Fluid Check processing is only associated with the laser controller. The main purpose of the fluid check feature is to shut off or interrupt the laser in case of a problem. The fluid may checked, for example, using three electro-mechanical switches that can be independently enabled or disabled. The three fluid check switches are Bubble, low Flow and Leak. Any or all of the enabled fluid switch inputs that get triggered (i.e., failure indication) will generate a flow status error and subsequently reduce power, shut off or interrupt the laser. The laser will remain this way until the failure is cleared.

Bubble Switch Processing

The bubble detection is performed utilizing the system's Auxiliary Interrupt. The interrupt is run at a 1 msec rate and loads a circular buffer of 100 elements with a dry or wet indication. Every update also checks the buffer for its total number of dry elements and number of dry contiguous elements. Different particle detection systems, for example UltraDI-20 and Chem-20, have different flow rates reflected in the different failure limits.

A reading & good-to-bad state transition occurs when:
Model A Total Dry Elements: >30
Model A Total Contiguous: >15
Model B Total Dry Elements: >14
Model B Total Contiguous: >7
A bad-to-good state transition occurs when a predetermined time period has passed after the first good reading is made.

Flow Switch Processing

The flow switch is assumed to be calibrated appropriately for this installation. A reading takes 1 second. A good-to-bad state transition will take approximately 2 seconds after the first bad reading is made. A bad-to-good state transition occurs when a predetermined time period has passed after the first good reading is made.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. An optical liquid particle counter system comprising:
a liquid particle counter comprising:
a flow chamber for flowing a liquid containing particles along a flow direction through a beam of electromagnetic radiation,
an optical source, in optical communication with said flow chamber, for providing said beam of electromagnetic radiation; and
an optical collection system for collecting and directing at least a portion of electromagnetic radiation onto a photodetector;
wherein said photodetector produces an electric signal characteristic of the number and/or size of said particles detected;
a fluid monitoring system in fluid communication with said flow chamber that detects bubbles in said liquid, a flow rate condition of said liquid, or both bubbles and a flow rate condition;
an actuator for engaging or disengaging an optical interrupter capable of redirecting, reshaping, or reducing the fluence of electromagnetic radiation from said optical source entering said flow chamber; and
a processor in operational communication with said fluid monitoring system and said actuator, wherein said processor receives monitoring data from said fluid monitoring system and provides a control signal to said actuator for engaging or disengaging said optical interrupter;
wherein said processor flags said monitoring data indicative of the presence of bubbles in said liquid as corresponding to a portion of the liquid in said flow chamber, and said control signal comprises timing instructions for actuating said optical interrupter at a time corresponding to passage of said portion of said liquid through said beam of electromagnetic radiation.

2. The optical liquid particle counter system of claim 1, wherein said control signal is provided by said processor when said processor analyzes said monitoring data and determines the presence of bubbles in said liquid, a flow rate condition of said liquid, or both bubbles and a flow rate condition.

3. The optical liquid particle counter system of claim 1, wherein said processor receives monitoring data from said fluid monitoring system and provides a control signal to said optical liquid particle counter or a component thereof to increase the power of said optical source to full operational power or to disengage said optical interrupter when said monitoring data indicates the absence of bubbles in said liquid, a normal flow rate condition of said liquid, or both.

4. The optical liquid particle counter system of claim 3, wherein during startup of said system, said optical liquid particle counter system will not provide power to said optical source until said processor receives said monitoring data from said fluid monitoring system indicating the absence of bubbles in said liquid, a normal flow rate condition of said liquid, or both.

5. The optical liquid particle counter system of claim 3, wherein said full operational power is greater than or equal to 20 mW, and said normal flow rate is less than or equal to 2000 mL/min.

6. The optical liquid particle counter system of claim 1, wherein said fluid monitoring system detects bubbles optically, electronically, acoustically, by pressure differential, by density, or a combination thereof.

7. The optical liquid particle counter system of claim 6, wherein said processor decreases said power of said optical source if said bubble has a diameter greater than or equal to the diameter of the particles being detected.

8. The optical liquid particle counter system of claim 1, wherein said fluid monitoring system detects a flow rate condition.

9. The optical liquid particle counter system of claim 8, wherein said flow rate condition is a high flow rate, a low flow rate, a normal flow rate or a flow stoppage.

10. The optical liquid particle counter system of claim 8, wherein said fluid monitoring system is a differential pressure flowmeter, a transit-time ultrasonic flowmeter, a rotameter/float sensor, a Doppler ultrasonic flow meter, a thermal mass flow meter, an electromagnetic flow meter, a turbine/paddle wheel meter, vortex flow meter, a flow switch, a Coriolis mass flow meter, a CCD or CMOS camera, or a combination thereof.

11. The optical liquid particle counter system of claim 1, wherein said flow rate condition corresponds to a normal flow rate and said processor provides a control signal to said actuator to disengage said optical interrupter.

12. The optical liquid particle counter system of claim 1 further comprising:
a liquid conditioner, wherein said liquid conditioner splits a fluid entering said liquid particle counter system into a sampling stream in fluid communication with said flow chamber and a bypass stream and promotes the removal of bubbles out of said sampling stream and into said bypass stream.

13. The optical liquid particle counter system of claim 12, wherein said liquid conditioner decreases a linear velocity of said liquid within said liquid conditioner with respect to the velocity of said liquid before or after said liquid conditioner.

14. The optical liquid particle counter system of claim 1, wherein said optical interrupter is a mirror, an optical filter, a polarization optical switch, a shutter, a beam dump, a beam expanding lens, a heat sink or a combination thereof.

* * * * *